United States Patent
Falling

(10) Patent No.: US 6,790,999 B1
(45) Date of Patent: Sep. 14, 2004

(54) PROCESS FOR THE PRODUCTION OF 3-BUTEN-1-OL

(75) Inventor: Stephen Neal Falling, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 50 days.

(21) Appl. No.: 10/377,425

(22) Filed: Feb. 28, 2003

(51) Int. Cl.[7] .................. C07C 27/00; C07C 29/00; C07C 32/02; C07C 27/18; C07C 29/10
(52) U.S. Cl. .................. 568/908; 568/876; 568/884; 568/885; 568/907
(58) Field of Search .................. 568/876, 884, 568/885, 907, 908

(56) References Cited

U.S. PATENT DOCUMENTS

| | | |
|---|---|---|
| 3,574,773 A | 4/1971 | Mueller et al. |
| 4,261,901 A | 4/1981 | Squire |
| 4,288,374 A | 9/1981 | Squire |
| 5,406,007 A | 4/1995 | Falling |
| 6,103,943 A | 8/2000 | McCombs |
| 6,262,262 B1 | 7/2001 | Kjell |

OTHER PUBLICATIONS

R. C. Larock et al, Tetrahedron Letters, vol. 30, No. 48, pp. 6629–6632 (1989).
J. Tsuji et al., Chemistry Letters, pp. 1017–1020 (1984).

Primary Examiner—Elvis O. Price
(74) Attorney, Agent, or Firm—Michael J. Blake; Bernard J. Graves, Jr.

(57) ABSTRACT

Disclosed is a process for the continuous, semi-continuous or batch production of 3-buten-1-ol from 3,4-epoxy-1-butene wherein 3,4-epoxy-1-butene and formic acid are fed to a reaction zone having a catalyst solution comprising a palladium(0) compound, a tertiary phosphine, a trialkylamine and an organic solvent. Preferably in the operation of this invention, 3-buten-1-ol product and reaction side products serve as the organic solvent for the process. The preferred mode of operation is continuous addition of reactants to the reaction mixture with simultaneous, continuous distillation of a reaction product comprising 3-buten-1-ol.

19 Claims, No Drawings

PROCESS FOR THE PRODUCTION OF 3-BUTEN-1-OL

PROCESS FOR THE PRODUCTION OF 3-BUTEN-1-OL

FIELD OF THE INVENTION

This invention pertains to a process for the preparation of 3-buten-1-ol from 3,4-epoxy-1-butene (EPB). More specifically, this invention pertains to the synthesis of 3-buten-1-ol by contacting EPB and formic acid with a catalyst solution comprising a palladium(0) compound, a tertiary phosphine and a tertiary amine.

BACKGROUND OF THE INVENTION

3-Buten-1-ol is an important intermediate in the production of pharmaceuticals. The palladium-catalyzed coupling of 3-buten-1-ol with aryl halides is a valuable process for the preparation of aryl-substituted aldehydes (R. C. Larock et al., *Tetrahedron Letters*, 30, 6629 (1989)). This coupling process is used in the production of antifoliate compound Pemetrexed disodium (U.S. Pat. No. 6,262,262).

U.S. Pat. No. 3,574,773 discloses the preparation of 3-buten-1-ol by reacting propylene with aqueous formaldehyde in the presence of a base such as ammonia at a temperature of 235 to 400° C. and a pressure of 50 to 500 atmospheres. U.S. Pat. Nos. 4,261,901 and 4,288,374 also describe the preparation of 3-buten-1-ol by reacting propylene and aqueous formaldehyde stabilized with an alcohol in the presence of silica sand at a temperature of 250 to 350° C. and a pressure of 50 to 800 atmospheres. A 27% conversion of formaldehyde to 3-buten-1-ol is reported in an example.

U.S. Pat. No. 5,406,007 discloses a process for preparing a mixture of 2-buten-1-ol (crotyl alcohol) and 3-buten-1-ol by the hydrogenation of EPB in the presence of a sulfur-modified or sulfided nickel catalyst.

J. Tsuji et al., *Chem. Letters*, 1017 (1984) disclose the homogeneous transfer hydrogenation of EPB to 3-buten-1-ol by heating a mixture of EPB, tris(dibenzylideneacetone)dipalladium(0)-chloroform adduct, tri-n-butylphosphine, ammonium formate and dioxane solvent at 100° C. for one hour. Ammonium formate is the source of hydrogen in this process and carbon dioxide is a by-product. The use of the Tsuji et al. process to manufacture 3-buten-1-ol on a commercial scale is not practical because of the toxicity of dioxane and chloroform (suspected carcinogens) and the production of a white solid during the operation of the process. This white solid is believed to be a mixture of ammonium formate and ammonium carbonate formed from ammonia and carbon dioxide derived from the ammonium formate. The white solid can foul and plug process equipment such as condensers which may lead to hazardous build up of pressure within the equipment and reactor.

U.S. Pat. No. 6,103,943 discloses a batch process for preparing 3-buten-1-ol from EPB on a commercial scale. In this process, EPB is converted to 3-buten-1-ol by contacting EPB and formic acid with a catalyst solution comprising a palladium(0) compound, a tertiary phosphine, and a trialkylamine in tetrahydrofuran (THF). At the conclusion of the process, the catalyst is normally deactivated by the addition of 30% hydrogen peroxide and/or cupric chloride. The deactivation of catalyst is said to be needed to prevent isomerization of product to 2-buten-1-ol during distillation of the product from the reaction mixture. This process has several serious drawbacks which result in inefficient and expensive production of 3-buten-1-ol. The single batch use of the expensive palladium(0) catalyst results in less than 6000 moles of 3-buten-1-ol per gram-atom palladium (catalyst turnovers). THF is an expensive solvent which must be removed by efficient fractional distillation. Deactivation of the palladium catalyst with cupric chloride results in a copper mirror on the inside surface of the reaction vessel which must be removed prior to the next batch. Removal of this mirror is a costly and hazardous process requiring the use of hot, aqueous nitric acid.

SUMMARY OF THE INVENTION

An improved process has now been discovered which permits, in addition to a batch mode of production, the continuous or semi-continuous production of 3-buten-1-ol from EPB. In batch, continuous or semi-continuous processes, EPB is converted to 3-buten-1-ol by addition of EPB and formic acid (reactants) to a catalyst solution comprising a palladium(0) compound, a tertiary phosphine, a tertiary amine and an organic reaction solvent. The continuous or semi-continuous process for the preparation of 3-buten-1-ol provided by the present invention comprises the steps of:

(1) feeding EPB and formic acid to a reaction zone containing a catalyst solution comprising a palladium (0) compound, a tertiary phosphine, a tertiary amine and an organic solvent, to form a reaction mixture, maintained at an elevated reaction temperature; and (2) distilling the contents of the reaction zone to remove a vapor comprising 3-buten-1-ol;

wherein the organic solvent comprises 3-buten-1-ol, an extraneous solvent having a boiling point of at least 130° C., or a mixture thereof.

As is discussed in further detail below, the foregoing process steps may be performed sequentially or in a substantially simultaneous manner. The continuous or semi-continuous process of the present invention allows the extended use of the expensive palladium(0) catalyst, and allows the product to be distilled from the reaction mixture with little or no product isomerization. Thus, in accordance with the present invention the catalyst may be used over extended periods of time to achieve greater than 30,000 catalyst turnovers resulting in improved efficiency and lower cost operation.

DETAILED DESCRIPTION

The EPB and formic acid reactants may be added simultaneously or in alternating portions. Typically, the reactants are added in EPB:formic acid mole ratios in the range of about 1.4:1 to about 0.9:1, more typically in the range of about 1.2:1 to about 1:1. The preferred mode of operation is simultaneous, continuous addition of both reactants with simultaneous, continuous distillation of 3-buten-1-ol and volatile side products. The formic acid used in the process may be provided as an aqueous solution of formic acid or as essentially pure formic acid, e.g., from about 70 to 100 weight percent formic acid. The water introduced into the system when aqueous formic acid solution is used does not substantially affect the catalyst system or its activity. However, for the purpose of product purification and to avoid or minimize the formation of product/water azeotropes, it is preferable to minimize the amount of water present in the reaction mixture by using an aqueous, formic acid solution comprising at least 88, preferably at least 95 weight percent formic acid.

The particular palladium(0) compound used is not critical and can be selected from various palladium(0) complexes such as tris(dibenzylideneacetone)-dipalladium(0), tris(dibenzylideneacetone)dipalladium(0)-chloroform complex, bis(dibenzylideneacetone)palladium(0), and tetrakis(triphenylphosphine)palladium(0). Palladium salts such as palladium(II) acetate, palladium(II) chloride, dichlorobis(benzonitrile)palladium(II), dichlorobis(acetonitrile)palladium(II), and palladium(II) acetylacetonate also may be used which are converted in situ or ex situ to palladium(0) complexes. The palladium(0) compound is present in the reaction mixture in the reaction zone in a catalytic amount, e.g., from about 0.001 to about 0.5 weight percent Pd based on the total weight of the reaction mixture. Palladium concentrations of about 0.01 to about 0.1 weight percent (same basis) are preferred.

The tertiary (trisubstituted) phosphine may be selected from a wide variety of trihydrocarbylphosphines wherein the total carbon content of the three hydrocarbyl (or hydrocarbon) groups, e.g., alkyl, cycloalkyl and aryl groups, ranges from 8 to 30 carbon atoms. The tertiary phosphine preferably is selected from triarylphosphines wherein the total carbon content of the aryl groups is in the range of 18 to 30. Examples of tertiary phosphines are triphenylphosphine, tri-ortho-tolylphosphine, tricyclohexylphosphine, tri-n-butylphosphine, tri-n-octylphosphine, and 1,2-bis(diphenylphosphino)ethane. Triphenylphosphine is particularly preferred. The amount of phosphine used in the present process should be an amount which gives a P:Pd atomic ratio of at least 2:1, preferably at least 3:1. Preferred phosphine concentrations provide P:Pd atomic ratios in the range of about 3:1 to about 12:1. Tertiary phosphines attached to a polymeric support such as polystyrene or a polyacrylic may be used in the invention. An example of a supported tertiary phosphine is triphenylphosphine bound to styrene-divinylbenzene copolymer (20% crosslinked) (available from Strem Chemicals, Inc.).

The tertiary amine employed in the process comprises one or more trisubstituted amines having a boiling point of at least 130° C., typically about 200 to about 250° C., to permit distillation of the product from the reaction zone without significant loss of the amine. The tertiary amine may contain a total of 9 to 30 carbon atoms. Preferred tertiary amines are selected from trialkylamines containing a total of 12 to 18 carbon atoms (total carbon atom content of the three alkyl groups). Specific examples of tertiary amines which may be used in the process include tri-n-butylamine, tri-n-hexylamine, di-n-octyl(methyl)amine, dimethyl(n-octyl)amine, tri-n-octylamine, N,N-dimethylaniline, and dicyclohexyl(ethyl)amine. Tri-n-butylamine is particularly preferred. The concentration of the tertiary amine in the reaction mixture may be in the range of about 5 to about 60 weight percent, preferably about 10 to about 50 weight percent, based on the total weight of the reaction mixture. Tertiary amines attached to a polymeric support such as polystyrene or a polyacrylic may be used in the invention. Examples of supported amines include Diaion WA10, Diaion WA30 (available from Mitsubishi Chemical America, Inc.) and Amberlyst A-21 (available from Rohm and Haas Co.).

The process is operated at elevated temperatures, typically in the range of about 70° C. to about 140° C. and preferably at or near the boiling point of the reaction mixture such as, for example, 90° C. to 130° C. Since the reaction is exothermic, heat usually must be removed from the reactor to control the process at the desired temperature range. Heat can be removed by means well known in the art, e.g., via a circulating heat transfer fluid in the reactor's jacket or heating/cooling coils. The process may be carried out at pressures moderately above or below ambient (atmospheric) pressure but normally is carried out at about ambient pressure. Operation of the process at about 90 to about 140° C. at about ambient pressure permits product 3-buten-1-ol to be vaporized from the reaction mixture as it is formed. Gaseous carbon dioxide is a reaction co-product and assists in the transport of 3-buten-1-ol and volatile side products from the reaction zone. A fractionation column on the reactor may be used to improve the separation of products from higher boiling tertiary amine, tertiary phosphine and optional high-boiling solvent.

The organic solvent employed in the process may be an extraneous solvent, preferably having a boiling point of about 130 to about 250° C. When an extraneous solvent is employed, essentially all of the high-boiling extraneous solvent remains in the reaction zone while 3-buten-1-ol and volatile side products are distilled. An example of an extraneous, high-boiling solvent is 2-methoxyethyl ether which boils at 162° C. Preferably, the organic solvent comprises 3-buten-1-ol. In this preferred mode of operation, 3-buten-1-ol is the product of reaction as well as the process organic solvent. A different solvent may be utilized during start-up of continuous operation. The optional start-up solvent preferably is a solvent which has a boiling point lower than 3-buten-1-ol and, therefore, is replaced by 3-buten-1-ol and reaction side products as the reaction proceeds and the start-up solvent is distilled from the reaction zone. The preferred optional start-up solvent is THF which has a boiling point of 67° C.

In continuous mode, the step of feeding the reactants to the reaction zone and the step of distilling are performed in a substantially simultaneous and continuous manner. That is, once the reaction has started, and thus begun to form product, reactants are continuously added as carbon dioxide is vented and a product comprising 3-buten-1-ol is continuously distilled. One of skill in the art will recognize, however, that temporary or minor interruptions during reactant addition and/or product recovery, such as might occur while managing the volume of the contents of the reaction zone, are normal during extended continuous operation.

Although continuous operation of the process of this invention is the most efficient mode of operation, the process also may be performed in semi-continuous or batch mode. In the semi-continuous mode, the reactants are added to the catalyst solution without simultaneous distillation of 3-buten-1-ol. Typically, carbon dioxide is vented while the reactants are added. After addition of the reactants is complete, the equipment is then operated in distillation mode to distill the reaction products. Heat may be supplied to, or removed from, the reaction zone by means known to those of skill in the art to maintain the temperature at a level sufficient to distill the volatile reaction products from the reaction zone. When most of the products have been distilled, the equipment is operated in reactant addition mode again. This alternating sequence of reactant addition and product recovery (e.g., distillation) can be repeated as many times as needed to produce the desired quantity of product or until catalyst activity has declined to an inefficient level.

In continuous and semi-continuous mode the occasional addition of a small amount of fresh palladium(0) catalyst, tertiary phosphine, and/or tertiary amine may be required in order to maintain needed concentrations in the reaction mixture. Likewise, occasional removal (purging) of a small amount of reaction mixture may be needed to give steady levels of high-boiling side products (high boilers) which accumulate in the reaction mixture. Without periodic purging, high boilers will, over long continuous operation, dilute the catalyst and fill the reactor.

The advantages provided by the present invention also may be achieved in batch operation of the process for producing 3-buten-1-ol. In this mode of operation, the organic solvent is 3-buten-1-ol, an extraneous high-boiling solvent, or a mixture thereof. In batch mode, the reactants are added to the catalyst solution with subsequent distillation to remove a product containing 3-buten-1-ol. The distillation can be performed in the same unit as the reaction or in another unit equipped for batch distillation. Typically, carbon dioxide is vented while the reactants are added. When 3-buten-1-ol is used as the organic solvent, it is recovered at the end of batch operation by distillation along with 3-buten-1-ol produced during reaction. Eliminating the use of THF as batch reaction solvent provides a more efficient and less costly batch operation. That is, it is preferred that the present process be run in the substantial absence of THF when operating in the batch mode.

Continuous, semi-continuous and batch operation of this invention can be accomplished with a single reactor vessel which is equipped for reactant addition as well as distillation. The evolution of carbon dioxide requires efficient condenser capability to condense volatile products from the gas/vapor stream. Continuous operation may be performed in equipment designs which are well known in the art such as with a single reactor or two or more sequential vessels, i.e., continuous stirred tank reactors (CSTR). Distillation of products from any mode of operation may be accomplished by distillation directly from the reactor, or by use of distillation systems well known in the art, e.g., one or more fractional distillation columns, wiped-film evaporators, or falling-film evaporators. These distillation systems may be operated externally from the reaction zone (i.e., external from the reactor(s) in which the reaction zone(s) reside) in which case they are continuously fed the liquid contents of the reaction zone. The resulting residue from distillation of all or most of the 3-buten-1-ol and volatile side products contains palladium(0) catalyst, tertiary phosphine, tertiary amine and organic solvent. For continuous or semi-continuous operation, this residue may be recycled to the reaction zone for further reaction usage or treated prior to recycle to, for example, remove high-boilers or replenish catalyst. Normally a crude, distilled product is recovered first followed by further purifying step(s), such as (i) treatment to remove aldehydes and/or (ii) fractional distillation to isolate purified product.

The major product obtained from the process of this invention is 3-buten-1-ol. However, 2-buten-1-ol (cis- and trans-crotyl alcohol) also is produced as a side product in lesser amount. The ratio of 3-buten-1-ol to 2-buten-1-ol typically is in the range of about 95:5 to about 75:25. Although the major product, 3-buten-1-ol, is the more valuable product economically, 2-buten-1-ol is also valuable and can be isolated during fractional distillation of the crude reaction distillate. Other volatile side products include crotonaldehyde (cis and trans isomers from isomerization of EPB), n-butanol, butyraldehyde, 3-buten-1-yl formate and 2-buten-1-yl formate (cis and trans isomers). High-boiling side products include 3,4-dihydroxy-1-butene (from hydrolysis of EPB), ethers resulting from addition of hydroxyl-containing products and side products to EPB, and formate esters of the aforementioned compounds.

Since crotonaldehyde cannot be separated easily from 3-buten-1-ol or 2-buten-1-ol by distillation, product isolation may be assisted by the addition of a primary amine or, preferably, a secondary amine to the crude reaction distillate. Such primary or secondary amines react with crotonaldehyde (and butyraldehyde) to form high-boiling products which are readily separable from 3-buten-1-ol and 2-buten-1-ol products. Morpholine and diethanolamine are particularly effective for this purpose. Crotonaldehyde removal also can be accomplished by the addition of an alkali metal hydroxide or carbonate, e.g., sodium hydroxide, to the crude reaction distillate to convert the crotonaldehyde to high boiling compounds.

Our novel process for the preparation of 3-buten-1-ol preferably is carried out in a continuous mode of operation comprising, following start-up, the steps of:

continuously feeding EPB and formic acid to a reaction zone containing a catalyst solution comprising a palladium(0) compound, a tertiary phosphine, a tertiary amine and an organic solvent maintained under boiling conditions; and continuously removing a vapor comprising 3-buten-1-ol and carbon dioxide from the reaction zone;

wherein the organic solvent comprises 3-buten-1-ol, an extraneous solvent having a boiling point of at least 130° C., or a mixture thereof.

Similarly, a semicontinuous mode of operating our process preferably would include the steps of:

(1) feeding EPB and formic acid to a reaction zone containing a catalyst solution comprising a palladium (0) compound, a tertiary phosphine, a tertiary amine and an organic solvent maintained at an elevated temperature; and (2) distilling the contents of the reaction zone to remove a vapor comprising 3-buten-1-ol;

wherein the organic solvent comprises 3-buten-1-ol, an extraneous solvent having a boiling point of at least 130° C., or a mixture thereof. In a semi-continuous mode, the steps of feeding and distilling are carried out, as described above, as substantially alternating steps.

When operating our process in a batch mode, the process would preferably comprise the steps of:

(1) contacting EPB and formic acid in a reaction zone containing a catalyst solution comprising a palladium (0) compound, a tertiary phosphine, a tertiary amine and an organic solvent, maintained at an elevated temperature; and (2) distilling the contents of the reaction zone to remove a vapor comprising 3-buten-1-ol;

wherein the organic solvent comprises 3-buten-1-ol, an extraneous solvent having a boiling point of at least 130° C., or a mixture thereof, and the process is carried out in the substantial absence of THF.

EXAMPLES

The process of the present invention is further illustrated by the following examples. Analytical results were determined by means of conventional gas chromatography (GC) procedures.

Example 1

Single Vessel Continuous Reaction

A 1000-mL, four-neck, round-bottom flask was equipped with a mechanical stirrer, thermocouple, heating mantle, Dean-Stark trap, efficient condenser, and Y-adapter with two 250-mL addition funnels. The condenser exit was connected to a bubbler to observe gas evolution. After purging the system with nitrogen, 200 mL (178 g) of tetrahydrofuran (THF) and 1.07 g (4.08 mmole) of triphenylphosphine were added to the flask. After the solids had dissolved, 0.24 g (0.26 mmole) of tris(dibenzylideneacetone)dipalladium(0) (Johnson Matthey) was added. After stirring a few minutes, 90 mL (0.38 mole) of tri-n-butylamine was added to the flask. To one of the addition funnels was added 130 mL (3.31 mole) of 96% formic acid. To the other addition funnel was added 250 mL (217.5 g, 3.10 mole) of 3,4-epoxy-1-butene (EPB). The reaction mixture was heated to about 62° C. then one-tenth of the formic acid charge was added to the flask. The EPB and remaining formic acid were added dropwise over 73 minutes. The reaction was exothermic and smoothly evolved carbon dioxide during the addition. The pot temperature was controlled with slight heating by a mantle in order to keep the mixture boiling and THF/products distilling while the reactants were being added (pot temperature 78-108° C., head temperature 66-89° C.). The Dean-Stark trap was used as the distillation head. The distillate take-off was adjusted to hold the reactor volume approximately constant. The collected distillate was a single layer and was water-white (weight 189 g). This first cycle yielded distillate which was mostly THF and the reaction solvent was replaced by products.

After the first cycle was complete, the addition funnels were immediately recharged with the same amount of reactants and a second cycle started. Eight cycles of the reaction were performed from one catalyst charge. The process details and results are summarized in Table 1 and other GC analysis results are shown in Table 2. The theoretical yield for the entire run is 1790 g. The total calculated weight of 3-buten-1-ol is 1405 g for a yield of 78.5%. A catalyst turnover ratio of 37,500 moles of 3-buten-1-ol per gram-atom palladium was achieved.

In Table 1, 84.9 weight percent of the distillate from the first cycle was THF, Temp is temperature in ° C., Addition Time is the time in minutes required for the addition of EPB and formic acid, Distillate is the amount in grams of distillate recovered during each cycle, GC is weight percent 3-buten-1-ol present in the distillate and Butenol is the amount in grams of 3-buten-1-ol present in the distillate based on the GC analysis. Triphenylphosphine (0.34 g) was added at the start of the eighth cycle. The Final Strip represents the final distillation to collect distillate after the addition of reactants EPB and formic acid was terminated.

Table 2 reports weight percentages (GC normalized weight percent) of other materials present in the distillate collected during each cycle. In Table 2, BuOH=1-butanol, HBu=butyraldehyde, EPB=3,4-epoxy-1-butene, H2O= water, HCr=cis- and trans-crotonaldehyde, CROH=cis- and trans-2-buten-1-ol, Bu3N=tri-n-butylamine, 3-Butenyl Formate=3-buten-1-yl formate, and 2-Butenyl Formate=cis- and trans-2-buten-1-yl formate.

TABLE 1

| Cycle | Pot Temp. | Head Temp. | Addition Time | Distillate | GC | Butenol |
|---|---|---|---|---|---|---|
| 1 | 78–108 | 66–89 | 73 | 189 | 9.41 | 17.8 |
| 2 | 106–109 | 89–99 | 66 | 191 | 83.2 | 159 |
| 3 | 104–108 | 92–99 | 118 | 188 | 86.5 | 163 |
| 4 | 103–112 | 99–106 | 143 | 204 | 87.7 | 179 |
| 5 | 108–115 | 99–105 | 154 | 217 | 87.2 | 190 |
| 6 | 109–114 | 94–108 | 126 | 228 | 86.6 | 198 |
| 7 | 105–112 | 105–107 | 151 | 231 | 82.8 | 192 |
| 8 | 101–116 | 96–105 | 141 | 203 | 74.1 | 151 |
| Final Strip | 120–151 | 118–127 | | 188 | 82.0 | 155 |
| Totals | | | | 1650 | | 1405 |

TABLE 2

| Cycle | BuOH | HBu | 3-Butenyl Formate | 2-Butenyl Formate | EPB | H2O | HCr | CrOH | Bu3N |
|---|---|---|---|---|---|---|---|---|---|
| 1 | 0.24 | 0 | 2.63 | 0.15 | 0.72 | 1.78 | 0 | 0 | 0 |
| 2 | 0 | 0.21 | 3.54 | 0 | 0.22 | 7.25 | 0.84 | 2.98 | 1.03 |
| 3 | 0 | 0.35 | 1.81 | 0 | 0.13 | 5.99 | 1.15 | 3.29 | 0.77 |
| 4 | 0.11 | 0.78 | 0 | 0 | 0 | 5.53 | 0.81 | 4.00 | 0.99 |
| 5 | 0.17 | 0.42 | 0.91 | 0 | 0.49 | 3.78 | 0.59 | 5.74 | 0.69 |
| 6 | 0.22 | 0.52 | 1.35 | 0 | 0.14 | 3.23 | 0.53 | 6.68 | 0.74 |
| 7 | 0.35 | 0.57 | 2.75 | 0.22 | 1.03 | 3.87 | 0.47 | 7.23 | 0.64 |
| 8 | 0.21 | 0.22 | 9.45 | 0.48 | 1.93 | 5.24 | 0.92 | 7.40 | 0 |
| Final Strip | 0.37 | 0.09 | 0.80 | 0.05 | 0 | 1.19 | 0.00 | 12.23 | 3.23 |

Example 2

Fractional Distillation

The distillates from the eight reaction cycles and the final strip of Example 1 were combined in a 2000-mL, three-neck, round-bottom flask equipped with a magnetic stirrer, thermocouple, heating mantle, insulated column packed with 56 cm (22 inches) of Penn State packing (ca. 11 theoretical stages), magnetically-controlled distillation head and condenser. To the crude mixture was added 42 mL (42 g, 0.48 mole) of morpholine. The mixture was heated to 80° C. then allowed to cool overnight. GC analysis showed complete removal of crotonaldehyde. The red mixture was heated to distill at atmospheric pressure. Distillation details are given in Table 3 and other GC analysis results are shown in Table 4. A small lower (aqueous) layer was observed in fractions 1 and 2. In Table 3, Temp is temperature in ° C., Reflux Ratio is the ratio of distillate returned to the distillation column to the distillate collected, Distillate is the amount in grams of distillate recovered for each fraction collected, % Butenol is the GC weight percent 3-buten-1-ol present in the distillate and Weight Butenol is the amount in grams of 3-buten-1-ol present in the distillate based on the GC analysis. Analyses of Fractions 1 and 2 are normalized area percentages of the top (organic) layer, Fraction 3-10 are normalized weight percentages, and Pot Residue (undistilled material) is unnormalized weight percentage. Table 4 reports weight percentages of other materials present in each distillate fraction collected. BuOH, H2O, CrOH, Bu3N, THF, 3-Butenyl Formate, and 2-Butenyl Formate have the meanings given above.

The theoretical yield for the continuous experiment of Example 1 run is 1790 g. The combined weight of fractions 4-8 is 1087 g of material having a 3-buten-1-ol content of 96.8% (58.8% yield).

TABLE 3

| Fraction | Pot Temp | Head Temp | Reflux Ratio | Distillate | % Butenol | Weight Butenol |
|---|---|---|---|---|---|---|
| 1 | 101–108 | 72–84 | 10/1 | 174 | 0.56 | 0.97 |
| 2 | 108–113 | 84–92 | 11/1 | 120 | 39.2 | 47.0 |
| 3 | 113–120 | 92–114 | 11/1 | 129 | 70.1 | 90.4 |
| 4 | 120 | 114–115 | 11/1 | 65.0 | 98.0 | 63.7 |
| 5 | 120–121 | 115 | 9/1 | 150 | 98.7 | 148 |
| 6 | 121–121 | 115 | 9/1 | 279 | 98.5 | 275 |
| 7 | 121–124 | 115–116 | 9/1 | 395 | 97.2 | 384 |
| 8 | 124–134 | 115–116 | 11/1 | 198 | 92.0 | 182 |
| 9 | 134–142 | 116–118 | 12/1 | 79.0 | 75.6 | 59.7 |
| 10 | 142–176 | 118–122 | 12/1 | 66.4 | 31.6 | 21.0 |
| Pot residue | | | | 168 | 0 | 0.0 |
| Total | | | | | | 1272 |

TABLE 4

| Fraction | BuOH | 3-Butenyl Formate | 2-Butenyl Formate | H2O | CrOH | Bu3N | THF |
|---|---|---|---|---|---|---|---|
| 1 | 0 | 0.29 | 0 | 79.4 | 0 | 0 | 19.4 |
| 2 | 0.13 | 14.9 | 0.68 | 21.9 | 0.16 | 0 | 22.6 |
| 3 | 0.12 | 3.68 | 0.21 | 24.0 | 0.37 | 0 | 1.42 |
| 4 | 0.12 | 0.83 | 0 | 0.41 | 0.64 | 0 | 0 |
| 5 | 0.13 | 0.31 | 0 | 0.10 | 0.78 | 0 | 0 |
| 6 | 0.15 | 0 | 0 | 0.08 | 1.24 | 0 | 0 |
| 7 | 0.22 | 0 | 0 | 0.07 | 2.48 | 0 | 0 |
| 8 | 0.29 | 0 | 0 | 0.10 | 7.64 | 0 | 0 |
| 9 | 0.42 | 0 | 0 | 0.13 | 22.8 | 0 | 0 |
| 10 | 0.13 | 0 | 0.12 | 0.16 | 67.9 | 0 | 0 |
| Pot residue | 0 | 0 | 0 | 0.06 | 13.6 | 15.4 | 0 |

Example 3

Continuous Stirred Tank Reactor Operation

Two 300-mL, three-neck, round-bottom flasks with side arms for liquid overflow operation were equipped with magnetic stirrers, thermocouples, heating mantles, and condensers. The condenser exits were connected to bubblers to observe gas evolution. The first flask (R1, 190 mL liquid volume) was placed so that it overflowed into the second flask (R2, 145 mL liquid volume) which overflowed into a two-inch diameter, wiped-film evaporator (WFE) operated at ambient pressure. Two pumps continuously fed EPB and 91% formic acid to R1 from reactant reservoirs on top-loading balances. The unevaporated residue from the WFE was continuously pumped back to R1 at a rate of about 7.2 mL/minute. The reaction mixture was prepared by dissolving 2.13 g (8.12 mmole) of triphenylphosphine in 320 mL (3.72 moles) of 3-buten-1-ol and 180 mL (0.756 moles) of tri-n-butylamine at 50° C. under nitrogen. When the solids had dissolved, 0.30 g (0.33 mmole) of tris(dibenzylideneacetone)dipalladium(0) (Johnson Matthey) was added and stirred until dissolved. The mixture was filtered into the nitrogen-purged reaction system to remove a small amount of insoluble black solids. The reactor contents were heated to about 98° C. and addition of EPB and formic acid reactants to R1 was begun. The addition of reactants is exothermic and little or no heating was needed for R1. Vigorous evolution of carbon dioxide from R1 is observed during reaction. The temperature of the reactors was generally held at 95-105° C. The jacket temperature of the WFE (95-120° C.) was adjusted as necessary to take off distillate at about the same rate of addition of EPB to R1. Table 5 shows reaction details and distillate GC analysis results during 26 hours of continuous operation. Time is the cumulative time in hours of operation, EPB Fed and Formic Acid Fed are the total amounts in grams of total EPB and formic acid fed at the given total time of operation, Distillate is the total amount of distillate collected from the WFE at the given total time of operation, and the values given for % Butenol, % HCr, % CrOH, % 3-Butenyl Formate and % Bu3N are GC area percentages (disregarding water) for 3-buten-1-ol, cis- and trans-crotonaldehyde, cis- and trans-2-buten-1-ol, 3-buten-1-yl formate and tributylamine, respectively, present in samples of distillate collected during the indicated increment of time of operation. The total calculated weight of 3-buten-1-ol is 1933 g for a yield of 85.8%. A catalyst turnover ratio of 40,900 moles of 3-buten-1-ol per gram-atom palladium was achieved.

TABLE 5

| Time | EPB Fed | Formic Acid Fed | Distillate | % Butenol | % HCr | % CrOH | % 3-Butenyl Formate | % Bu3N |
|---|---|---|---|---|---|---|---|---|
| 4.5 | 244 | 179 | 382 | 82.7 | 1.82 | 7.97 | 0.52 | 6.99 |
| 6.25 | 332 | 243 | 463 | 82.4 | 2.01 | 8.87 | 0.49 | 6.02 |
| 13.75 | 819 | 591 | 1029 | 79.6 | 1.83 | 11.8 | 1.61 | 5.19 |
| 18 | 1393 | 1005 | 1704 | 80.5 | 1.73 | 11.8 | 2.14 | 3.88 |
| 26 | 2190 | 1587 | 2456 | 74.0 | 0.64 | 11.8 | 10.7 | 1.44 |

The invention has been described in detail with particular reference to preferred embodiments thereof, but it will be understood that variations and modifications can be affected within the spirit and scope of the invention.

What is claimed is:

1. Process for the preparation of 3-buten-1-ol comprising:
   (1) feeding 3,4-epoxy-1-butene (EPB) and formic acid to a reaction zone containing a catalyst solution comprising a palladium(0) compound, a tertiary phosphine (p)

a tertiary amine and an organic solvent, to form a reaction mixture, maintained at an elevated reaction temperature; and (2) distilling the contents of the reaction zone to remove a vapor comprising 3-buten-1-ol;

wherein the organic solvent is selected from the group consisting of 3-buten-1-ol, an extraneous solvent having a boiling point of at least 130° C., or a mixture thereof.

2. Process according to claim 1 wherein EPB and formic acid are fed in an EPB:formic acid mole ratio of about 1.4:1 to about 0.9:1; the palladium(0) compound is present in the reaction mixture in an amount that provides a Pd concentration of about 0.001 to about 0.5 weight percent, based on the total weight of the reaction mixture; the tertiary phosphine has a total carbon content of 8 to 30 and is present in an amount that provides a P:Pd atomic ratio of at least 2:1; the tertiary amine is a trialkyl amine containing a total of 9 to 30 carbon atoms and having a boiling point of at least 130° C.; and the process is carried out at a temperature of about 70 to about 140° C.

3. Process according to claim 2 wherein EPB and formic acid are fed in an EPB:formic acid mole ratio of about 1.2:1 to about 1:1; the palladium(0) compound is present in the reaction mixture in an amount that provides a Pd concentration of about 0.01 to about 0.1 weight percent, based on the total weight of the reaction mixture; the tertiary phosphine has a total carbon content of 8 to 30 and is present in an amount that provides a P:Pd atomic ratio in the range of about 3:1 to about 12:1; the tertiary amine is a trialkyl amine containing a total of 12 to 18 carbon atoms; and the concentration of the tertiary amine in the reaction mixture is about 10 to about 50 weight percent, based on the total weight of the reaction mixture.

4. Process according to claim 3 wherein the tertiary phosphine is triphenylphosphine and the tertiary amine is tri-n-butylamine.

5. Process according to claim 1 wherein the process steps are performed in a continuous and substantially simultaneous manner and the contents of the reaction zone are maintained at a temperature of about 70 to about 140° C.

6. Process for the continuous preparation of 3-buten-1-ol comprising:

(1) continuously feeding EPB and formic acid to a reaction zone containing a catalyst solution comprising a palladium(0) compound, a tertiary phosphine (p), a tertiary amine and an organic solvent, to form a reaction mixture, maintained an elevated temperature; and (2) continuously distilling the contents of the reaction zone to remove a vapor comprising 3-buten-1-ol;

wherein the organic solvent comprises 3-buten-1-ol, an extraneous solvent having a boiling point of at least 130° C., or a mixture thereof.

7. Process according to claim 6 wherein EPB and formic acid are fed in an EPB:formic acid mole ratio of about 1.4:1 to about 0.9:1; the palladium(0) compound is present in the reaction mixture in an amount that provides a Pd concentration of about 0.001 to about 0.5 weight percent, based on the total weight of the reaction mixture; the tertiary phosphine has a total carbon content of 8 to 30 and is present in an amount that provides a P:Pd atomic ratio of at least 2:1; the tertiary amine is a trialkyl amine containing a total of 9 to 30 carbon atoms and having a boiling point of at least 130° C.; and the process is carried out at a temperature of about 70 to about 140° C.

8. Process according to claim 7 wherein EPB and formic acid are fed in an EPB:formic acid mole ratio of about 1.2:1 to about 1:1; the palladium(0) compound is present in the reaction mixture in an amount that provides a Pd concentration of about 0.01 to about 0.1 weight percent, based on the total weight of the reaction mixture; the tertiary phosphine has a total carbon content of 8 to 30 and is present in an amount that provides a P:Pd atomic ratio in the range of about 3:1 to about 12:1; the tertiary amine is a trialkyl amine containing a total of 12 to 18 carbon atoms; and the concentration of the tertiary amine in the reaction mixture is about 10 to about 50 weight percent, based on the total weight of the reaction mixture.

9. Process according to claim 8 wherein the tertiary phosphine is triphenylphosphine and the tertiary amine is tri-n-butylamine.

10. Process for the continuous preparation of 3-buten-1-ol comprising:

feeding EPB and formic acid to a reaction zone containing a catalyst solution comprising a palladium(0) compound, a tertiary phosphine, a tertiary amine and an organic solvent;

maintaining the contents of the reaction zone at an elevated temperature; and distilling to remove a vapor comprising a crude 3-buten-1-ol reaction product, wherein the organic solvent is selected from the group consisting of 3-buten-1-ol, an extraneous solvent having a boiling point of at least 130° C., or a mixture thereof.

11. Process according to claim 10 the tertiary phosphine is triphenylphosphine and the tertiary amine is tri-n-butylamine.

12. Process according to claim 10 wherein the contents of the reaction zone are maintained at a temperature of about 70 to about 140° C.

13. Process according to claim 10 wherein the process further comprises the step of purifying the crude 3-buten-1-ol reaction product by fractional distillation.

14. A batch process for the production of 3-buten-1-ol, which comprises:

(1) contacting EPB and formic acid in a reaction zone in the presence of a catalyst solution comprising a palladium(0) compound, a tertiary phosphine (p), a tertiary amine and an organic solvent, to form a reaction mixture, maintained at elevated temperature; and (2) distilling the contents of the reaction zone to remove a vapor comprising 3-buten-1-ol;

wherein the organic solvent comprises 3-buten-1-ol, an extraneous solvent having a boiling point of at least 130° C., or a mixture thereof, and the process is carried out in the substantial absence of THF.

15. Process according to claim 14 wherein the palladium (0) compound is present in an amount that provides a Pd concentration of about 0.01 to about 0.1 weight percent, based on the total weight of the reaction mixture; the tertiary phosphine is triphenylphosphine; and the tertiary amine is tri-n-butylamine.

16. Process according to claim 15 wherein the tertiary phosphine is present in an amount that provides a P:Pd atomic ratio in the range of about 3:1 to about 12:1, and the amount of tertiary amine present in the reaction mixture is about 10 to about 50 weight percent, based on the total weight of the reaction mixture.

17. Process for the continuous preparation of 3-buten-1-ol, comprising:

continuously feeding EPB and formic acid to a reaction zone containing a catalyst solution comprising a palladium(0) compound, a tertiary phosphine, a tertiary amine and an organic solvent, to form a reaction mixture, maintained under boiling conditions; and continuously removing a vapor comprising 3-buten-1-ol and carbon dioxide from the reaction zone;

wherein the organic comprises 3-buten-1-ol, an extraneous solvent having a boiling point of at least 130° C., or a mixture thereof.

18. Process according to claim 17 wherein the palladium (0) compound is present in an amount that provides a Pd concentration of about 0.01 to about 0.1 weight percent, based on the total weight of the reaction mixture; the tertiary phosphine is triphenylphosphine; and the tertiary amine is tri-n-butylamine.

19. Process according to claim 17 wherein the tertiary phosphine is present in an amount that provides a p:pd atomic ratio in the range of about 3:1 to about 12:1, and the amount of tertiary amine present in the reaction mixture is about 10 to about 50 weight percent, based on the total weight of the reaction mixture.

* * * * *

UNITED STATES PATENT AND TRADEMARK OFFICE
CERTIFICATE OF CORRECTION

PATENT NO.     : 6,790,999 B1
DATED          : September 14, 2004
INVENTOR(S)    : Falling It is certified that error appears in the above-identified patent and that said Letters Patent is hereby corrected as shown below:

Column 11,
Line 48, after "maintained" insert -- at --.

Column 12,
Line 67, after "phosphine" insert -- (P) --.

Column 13,
Line 5, after "organic" insert -- solvent --.

Signed and Sealed this

Twenty-second Day of March, 2005

JON W. DUDAS
*Director of the United States Patent and Trademark Office*